(12) United States Patent
Park et al.

(10) Patent No.: US 8,969,079 B2
(45) Date of Patent: Mar. 3, 2015

(54) METHOD FOR INDUCING HUMAN BLOOD-BORN HEMATOSPHERES THROUGH AGGREGATE CULTURE AND EXPANDING BLOOD ADULT STEM CELLS AND PROGENITOR CELLS, AND STEM CELL PREPARED BY THE SAME

(75) Inventors: Young-Bae Park, Seoul (KR); Hyo-Soo Kim, Seoul (KR); Hyun-Jae Kang, Seoul (KR); Hyun-Jai Cho, Seoul (KR); Jin Hur, Seoul (KR); Jong-Han Park, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 0 days.

(21) Appl. No.: 13/819,409

(22) PCT Filed: Aug. 8, 2011

(86) PCT No.: PCT/KR2011/005762
§ 371 (c)(1),
(2), (4) Date: Feb. 27, 2013

(87) PCT Pub. No.: WO2012/026687
PCT Pub. Date: Mar. 1, 2012

(65) Prior Publication Data
US 2013/0164841 A1    Jun. 27, 2013

(30) Foreign Application Priority Data
Aug. 27, 2010  (KR) .......... 10-2010-0083482

(51) Int. Cl.
*C12N 5/0789* (2010.01)
*C12N 5/078* (2010.01)

(52) U.S. Cl.
CPC ............ *C12N 5/0647* (2013.01); *C12N 5/0634* (2013.01); *C12N 2502/1157* (2013.01); *C12N 2513/00* (2013.01)
USPC ....................................................... 435/372

(58) Field of Classification Search
CPC ............. C12N 5/0647; C12N 2513/00; C12N 2502/1157; C12N 5/0634
See application file for complete search history.

(56) References Cited

U.S. PATENT DOCUMENTS

2005/0186672 A1 * 8/2005 Mahadeorao et al. ........ 435/368

FOREIGN PATENT DOCUMENTS

IT    WO2008/034740    * 3/2008 ............... C12N 5/06

OTHER PUBLICATIONS

Habich et al., Early appearance of stem/progenitor cells with neural-like characteristics in human cord blood mononuclear fraction cultured in vitro, Experimental Hematology, 34 (2006) 914-925.*

GE Healthcare, Ficoll-Paque PLUS, Instructions 71-7167-00 AG, Cell Preparation, Available online at: www.gelifesciences.com/gehcls_images/GELS/Related%20Content/Files/1314729545976/litdoc71716700AG_20110830221438.pdf, 2007, p. 1-16.*
GE Healthcare, T cell Expansion with Xuri™ systems, Isolation and Cultivation Protocol, Available online at: www.gelifesciences.com/gehcls_images/GELS/Related%20/Content/Files/1407251443213/litdoc29112375_20140805231637.pdf, 2014, p. 1-2.*
Case et al., "Human CD34+ AC133+ VEGFR-2+ cells are not endothelial progenitor cells but distinct, primitive hematopoietic progenitors", Experimental Hematology, vol. 35, pp. 1109-1118 (2007).
Suuronen et al., "Generation of CD133+ cells from CD133-peripheral blood mononuclear cells and their properties", Cardiovascular Research, vol. 70, pp. 126-135 (Mar. 10, 2006).
Peichev et al., "Expression of VEGFR-2 and AC133 by circulating human CD34+ cells identifies a population of functional endothelial precursors", Blood, vol. 95, pp. 952-958 (2000).
Kwon et al., "Suspension culture of hematopoietic stem cells in stirred bioreactors", Biotechnology Letters, vol. 25, pp. 179-182 (2003).
Ogawa et al., "Suspension culture of human mast cells/basophils from umbilical cord blood mononuclear cells", Proceedings of the National Academy of Sciences, vol. 80, pp. 4494-4498 (Jul. 1983).
Hur et al., "Human peripheral blood-born hematosphere as a niche for hematopoietic stem cell expansion", Cell Research, vol. 21, pp. 987-990 (Apr. 12, 2011).
Forraz, N. et al. "Characterization of a Lineage-Negative Stem-Progenitor Cell Population Optimized for Ex Vivo Expansion and Enriched for LTC-IC", Stem Cell, vol. 22, pp. 100-108(2004).
Peerani R, Zandstra PW. Enabling stem cell therapies through synthetic stem cell-niche engineering. Journal of Clinical Investigation. 2010; 120: 60-70.
Caldwell MA, He X, Wilkie N, et al. Growth factors regulate the survival and fate of cells derived from human neurospheres. Nat Biotech. 2001; 19: 475-479.
Messina E, De Angelis L, Frati G, et al. Isolation and expansion of adult cardiac stem cells from human and murine heart. Circ Res. 2004; 95: 911-921.
Aleksandra Habich, at al., "Early appearance of stem/progenitor cells with neural-like characteristics in human cord blood mononuclear fraction cultured in vitro", 2006 Experimental Hematology 34 (2006) 914-925.
I. Galan, et al., "Effect of a bone marrow microenviornment on the ex-vivo expansion of umbilical cord blood progenitor cells", Intl. Jnl. Lab. Hem. 2007, 29, 58-63.
Ana Paul D.N. de Barros, at al., "Osteoblasts and bone marrow mesenchymal stromal cells control hematopoletic stem cell migration and prolliferation in 3D in vitro model", 2010 Plos One, Feb. 2010, vol. 5, Issue 2, e9093, pp. 1-13.
European Search Report re PCT/KR2011005762, 2012.

* cited by examiner

*Primary Examiner* — Karen Cochrane Carlson
*Assistant Examiner* — Jennifer M. H. Tichy
(74) *Attorney, Agent, or Firm* — Lucas & Mercanti, LLP (57) ABSTRACT

The present invention relates to a technique of using monocytic blood cells to effectively culture and proliferate blood adult stem cells and progenitor cells that only exist in small quantities to effectively obtain large quantities of stem cells. According to the present invention, the limitation of being able to derive only small quantities of stem cells from blood can be overcome, and the pluripotency of stem cells can easily be obtained.

5 Claims, 9 Drawing Sheets

Umbilical cord blood-derived hematospheres

G-CSF mobilized hematospheres

METHOD FOR INDUCING HUMAN BLOOD-BORN HEMATOSPHERES THROUGH AGGREGATE CULTURE AND EXPANDING BLOOD ADULT STEM CELLS AND PROGENITOR CELLS, AND STEM CELL PREPARED BY THE SAME

CROSS-REFERENCE TO RELATED APPLICATIONS

This application is a 371 of PCT/KR2011/005762, filed on Aug. 8, 2011, which claims the benefit of Korean Patent Application No., 10-2010-0083482 filed on Aug. 27, 2010, respectfully, the contents of each of which are incorporated herein by reference.

TECHNICAL FIELD

The present invention relates to a technique to obtain large quantities of blood adult stem cells and progenitor cells by using blood mononuclear cells to effectively culture and proliferate blood adult stem cells and progenitor cells that only exist in small quantities.

BACKGROUND ART

The term "stem cells" is a generic name for cells that can differentiate into diverse specialized cell types and are found undifferentiated in embryos, fetuses, and adults. Among stem cells, blood adult stem cells which are derived from bone marrow refer to the stem cells with pluripotency that can differentiate into all kind of cells constituting organs and blood of human body.

Bone marrow-derived stem cells are considered as the ultimate therapeutic means for blood cancer, lymphoma, and bone marrow failure, but there is a difficulty in harvesting the bone marrow. To surmount this difficulty, a G-CSF injection has recently been used to mobilize stem cells from bone marrow into blood. However, G-CSF itself has the potential to cause side effects. On the other hand, stem cells are also derived from umbilical cord blood and deposited in a frozen form with cord blood banks. Umbilical cord blood-derived stem cells are actively studied, but quantitatively limited. Under these situations, it is very important to develop a method of obtaining a sufficient number of blood adult stem cells.

Conventional methods of expanding blood adult stem cells in vitro are, for the most part, directed towards the establishment of bone marrow-mimic environments with artificial substances, and are, in part, successful (Peerani R, Zandstra P W. Enabling stem cell therapies through synthetic stem cell-niche engineering. *Journal of Clinical Investigation.* 2010; 120: 60-70.). However, because the bone marrow, the source of blood adult stem cells, provides contacts with various supporting-cells and contains cytokines released from the cells and an extracellular matrix, it is difficult to establish a mimic environment sufficient to expand blood adult stem cells using artificial substances.

Meanwhile, some research and development groups in the study of stem cell derived from adult tissue have succeeded in developing techniques of expanding number of stem cells or maintaining the pluripotency of stem cells derived from heart or brain tissues by spheroid culture systems (Caldwell M A, He X, Wilkie N, et al. Growth factors regulate the survival and fate of cells derived from human neurospheres. Nat Biotech. 2001; 19: 475-479; and Messina E, De Angelis L, Frati G, et al. Isolation and expansion of adult cardiac stem cells from human and murine heart. Circ Res. 2004; 95: 911-921.).

Leading to the present invention, intensive and thorough research into the in vitro expansion of blood adult stem cells, aiming to overcome the problems encountered in the prior art, resulted in the development of human blood born-hematospheres culture to simply expand blood adult stem cells without losing their pluripotency.

DISCLOSURE

Technical Problem

It is an object of the present invention to provide a method for expanding blood adult stem cells in large quantities in vitro, which can overcome the vexation and potential side effects that may take place upon bone marrow harvesting and mobilization of stem cells into peripheral blood by G-CSF injection and the limited amount of umbilical cord blood-derived stem cells, thereby minimizing the problem of the shortage of cell supply.

It is another object of the present invention to provide blood adult stem cells which are capable of differentiating into all blood cell types and various cells of other tissues depending on the culture condition, and are effective for therapeutic uses.

Technical Solution

In order to accomplish the above objects, the present invention provides a method for expanding blood adult stem cells using human blood-born hematospheres while maintaining or improving the pluripotency of the cultured stem cells. In addition, the present invention suggests the use of the stem cells prepared according to the method in the therapy of blood diseases.

Advantageous Effects

When blood mononuclear cells organize into blood-born hematosphres, blood adult stem cells can reside and proliferate within the blood-born hematospheres, with their potency maximized. Because it can be performed in vitro, this method can be a solution to the ethical and economic problems that may take place upon repeated bone marrow harvesting and mobilization by G-CSF injection.

BEST MODE

Below, a description will be given of preferred embodiments of the present invention in conjunction with the accompanying drawings. It should be apparent to those skilled in the art that although many specified elements such as concrete components are elucidated in the following description, they are intended to aid the general understanding of the invention and the present invention can be implemented without the specified elements. Further, in the description of the present invention, when it is determined that the detailed description of the related art would obscure the gist of the present invention, the description thereof will be omitted. One skilled in the art will appreciate that although specific embodiments of the location system are described herein for purposes of illustration, various modifications may be made without deviating from the spirit and scope of the invention.

In the context of this disclosure, the terms "blood adult stem cells," "blood-born hematosphere (BBHS)," "adult cells," and "differentiation" are used. Unless stated otherwise, the following definitions apply.

The term "blood adult stem cells" refers to pluripotent cells in blood circulation, originating from the bone marrow, which can spontaneously differentiate into all cell types of blood and can be induced to differentiate into various cells of other tissues in response to a suitable stimulus.

The term "blood-born hematosphere (BBHS)" refers to an aggregate of blood mononuclear cells and certain cells having stemness, which form a three-dimensional structure, appearing spherical like an internal cell mass in a blastocyst.

The term "adult cells" refers to cells derived from a body after birth, as opposed to embryonic cells.

The term "differentiation" means the structural or functional specialization of cells during division, proliferation and growth of cells. That is, cells in a differentiation state undergo a morphological and functional change suitable to perform a mission given thereto. Generally speaking, differentiation is the process by which a less specialized cell becomes a more specialized cell. Alternatively, differentiation refers to the state in which a qualitative difference occurs between almost homogeneous parts in a biological system, or as a result, differential parts that are qualitatively discriminated therebetween are divided. For example, a multicellular organism in ontogenesis changes from a simple zygote to a complex system of tissues and cell types in which the head and the trunk, or myocytes and neural cells, are discriminated from each other.

Figure 1:
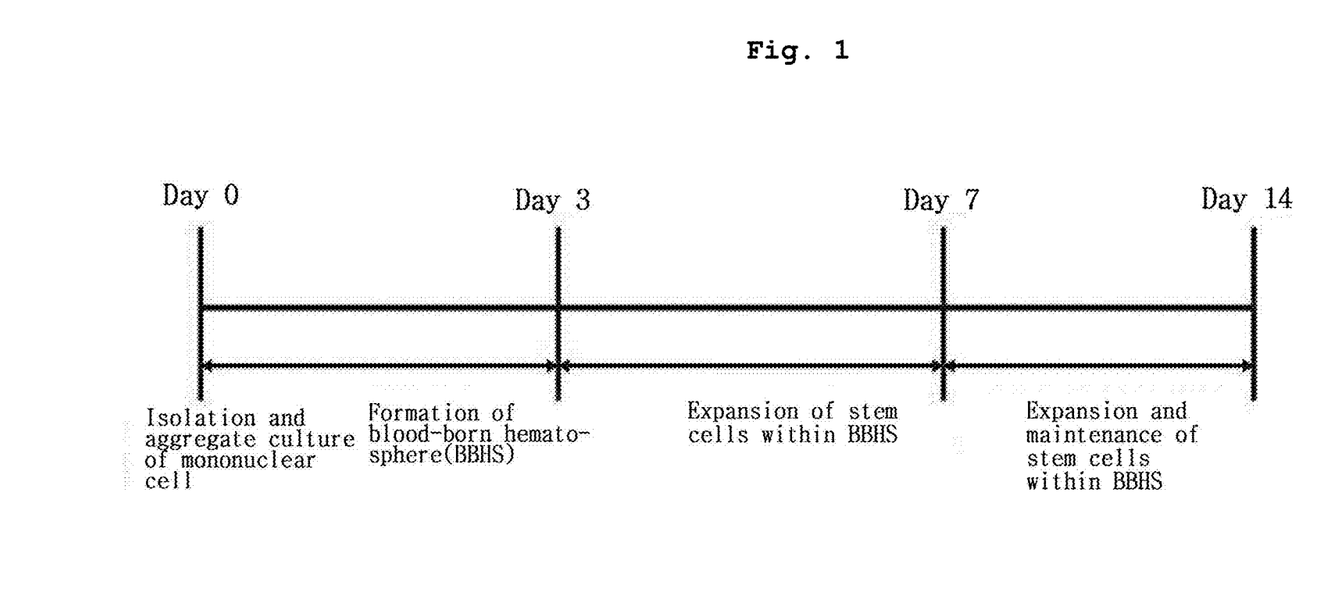
FIGS. 1 to 5 show the culture and preparing process of human blood-born hematospheres (BBHS) by a high-density aggregate culture of mononuclear cells isolated from human blood.
Figure 2:
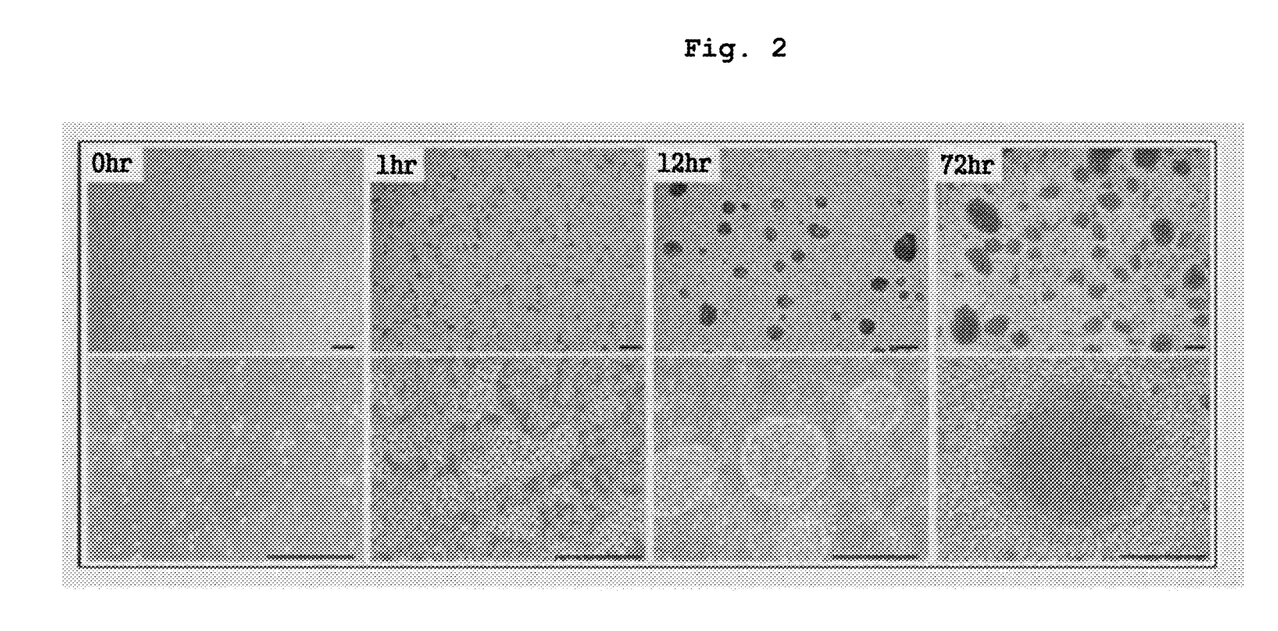
Figure 3:
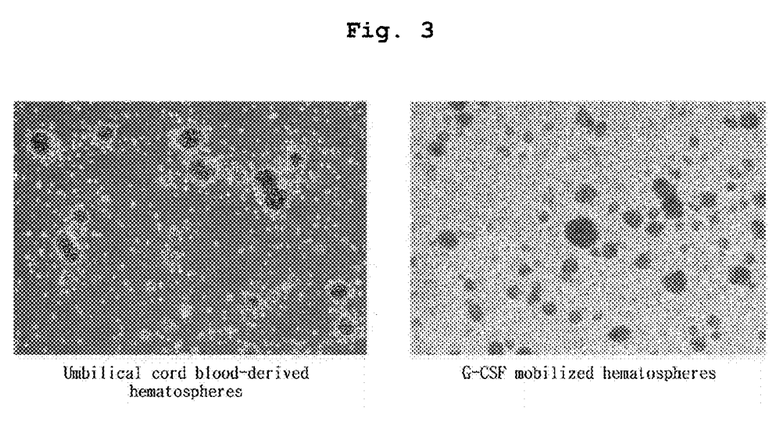
Figure 4:
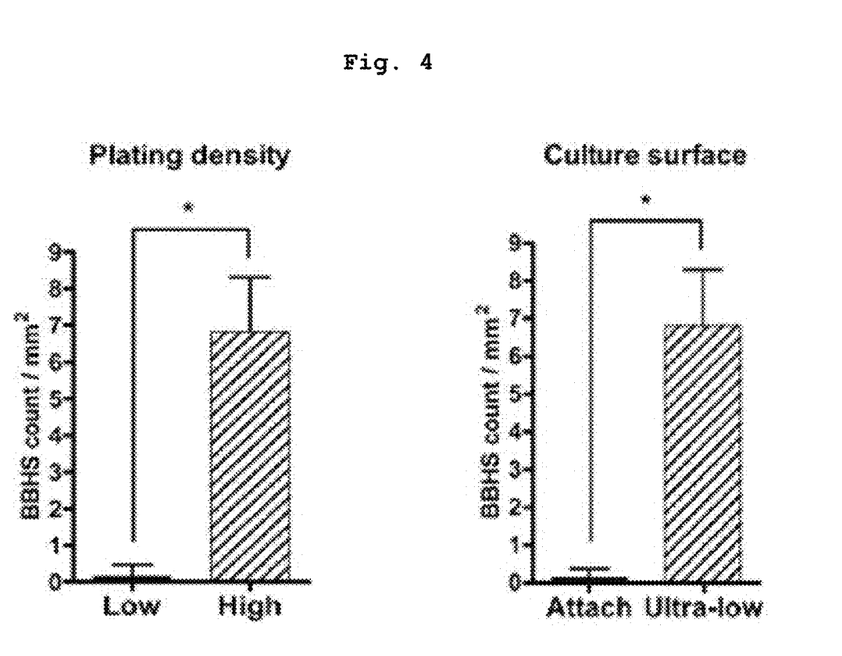
Figure 5:
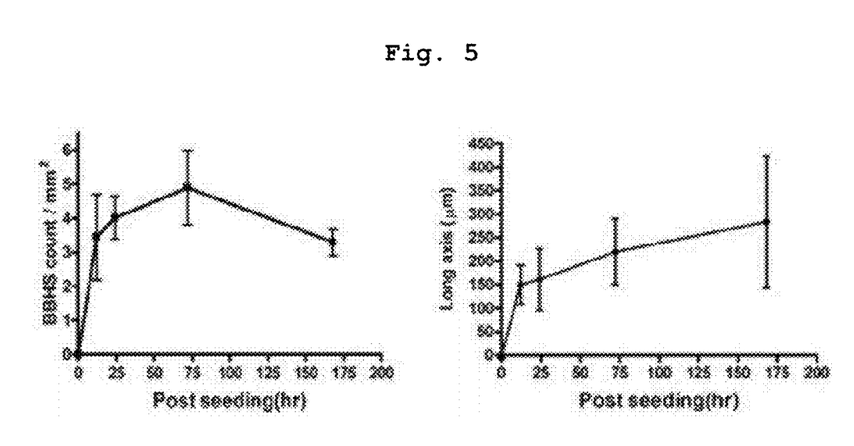

FIGS. 1 to 5 show the culture and preparing process of blood-born hematospheres (BBHS) by a high-density aggregate culture of mononuclear cells isolated from human blood. FIG. 1 is a schematic schedule for culturing human blood-born hematospheres and expanding blood adult stem cells. FIG. 2 shows morphological changes of human blood-born hematospheres with a high-density culture method and time. FIG. 3 shows morphologies of umbilical cord blood-derived hematospheres and G-CSF-mobilized hematospheres. FIG. 4 shows changes in BBHS count according to cell density and culture surface. FIG. 5 shows changes in BBHS count and size with culturing time.

In accordance with the present invention, the method for inducing human blood-born hematospheres through aggregate culture and for expanding blood adult stem cells and progenitor cells using the human blood-born hematospheres, comprises isolating mononuclear cells from blood; aggregate culturing of the isolated cells in a three-dimensional structure; proliferating the three-dimensionally cultured cells for a long period of time to form blood-born hematospheres; and dissociating the blood-born hematospheres into single cells. The method of the present invention will be explained in a stepwise manner with reference to FIGS. 1 to 5.

1) Step 1: Isolation of Mononuclear Cells from Blood

From various types of bloods cells, only mononuclear cells are isolated using density-gradient centrifugation. In detail, 10 ml of blood is diluted in 25 ml of PBS (phosphate buffered saline) at room temperature to prevent blood coagulation, and 35 ml of the dilution is carefully placed on 12 ml of Ficoll-Paque™ PLUS (GE healthcare). Following centrifugation at room temperature for 30 min at 400×g with a brake off, the mononuclear layer is picked up with care.

2) Step 2: Three-dimensional Aggregate Culture of Isolated Cells

The isolated cells are washed to remove substances used in the density gradient centrifugation and other blood residuals. In this regard, the cells are washed with 50 ml of PBS per 10 ml of the initial blood sample, and then spun down to remove blood residuals and platelets. The washing process is repeated five times at room temperature with a brake off, followed by respective spinning-down steps in a gradually decreasing speed order of 1,900-1,800-1,700-1,600-1,500 rpm. After completion of the washing process, the cells are resuspended in EBM (Lonza) free of serum or supplemented with 5% FBS, or in a cell culture medium free of animal-derived components selected from the group consisting of Stemline II (Sigma-Aldrich), Stempro34 (Invitrogen), and mTeSR®1 (STEMCELL Technologies).

In this context, the cell density must be $3~5\times10^6$ cells/ml. Given a lower cell density, the cells experience only an insufficient cell-to-cell contact, so that they cannot sufficiently aggregate together nor subsequently organize into spheres.

Preferably, the cell suspension is cultured in an ultra-low attach culture dish. When the dish is 60 mm in diameter, the cells are seeded in an amount of $2~3\times10^7$ cells in at least 6 ml of a medium to allow enough suspension. In a general culture dish or a plastic dish, cells do not organize into spheres, but adhere to the bottom.

Then, about $1\times10^8$ mononuclear cells can be obtained from 50 ml of blood.

3) Step 3: Proliferation of three-dimensionally cultured cells for a long period of time The mononuclear cells, when subjected to a high-density aggregate culture for 3 days in step 2, organize into human blood-born hematospheres with a size of 50~100 μm. The blood-born hematospheres increase in count until day 3, but in size until day 7 (FIG. 5). In this condition, a total of 80,000~120,000 blood-born hematospheres can be obtained from 50 ml of blood. The blood-born hematospheres were found to be maintained for 30 days if the same culture medium as used in the initial culture is added dropwise in an amount of 0.5~1 ml every other day. In the cell culture dish, cells that exist within the spheres are in mixture with single floating cells. Blood adult stem cells are contained and proliferated within the blood-born hematospheres.

4) Step 4: Dissociation of Blood-Born Hematospheres into Single Cells

For use in assay or therapy, the stem cells and progenitor cells expanded by the culture method must be dissociated from blood-born hematospheres. The hematospheres are spun down at 1,500 rpm for 10 min in tubes, and the resulting pellets are exposed to PBS containing 0.125% trypsin-EDTA and 0.5 mg/ml dispase at 37° C. for 5 min to dissociate the spheres into single cells, followed by harvesting by centrifugation. The spheres must be handled with care until the extracellular matrix is degraded by enzymes.

Figure 6:
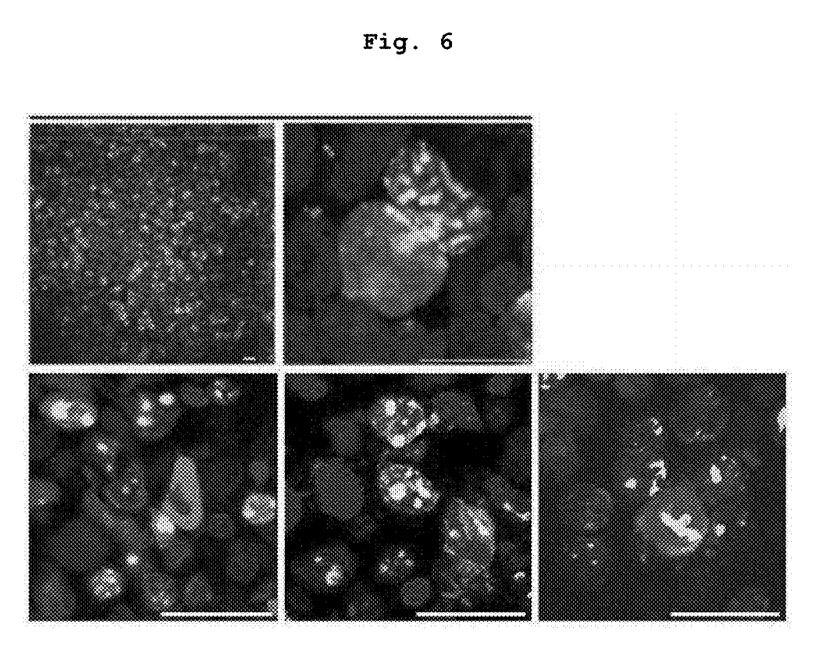
FIGS. 6 and 7 show the increase of cells positive to the marker of blood adult stem cells within the human blood-born hematospheres cultured according to the method of the present invention.
Figure 7:
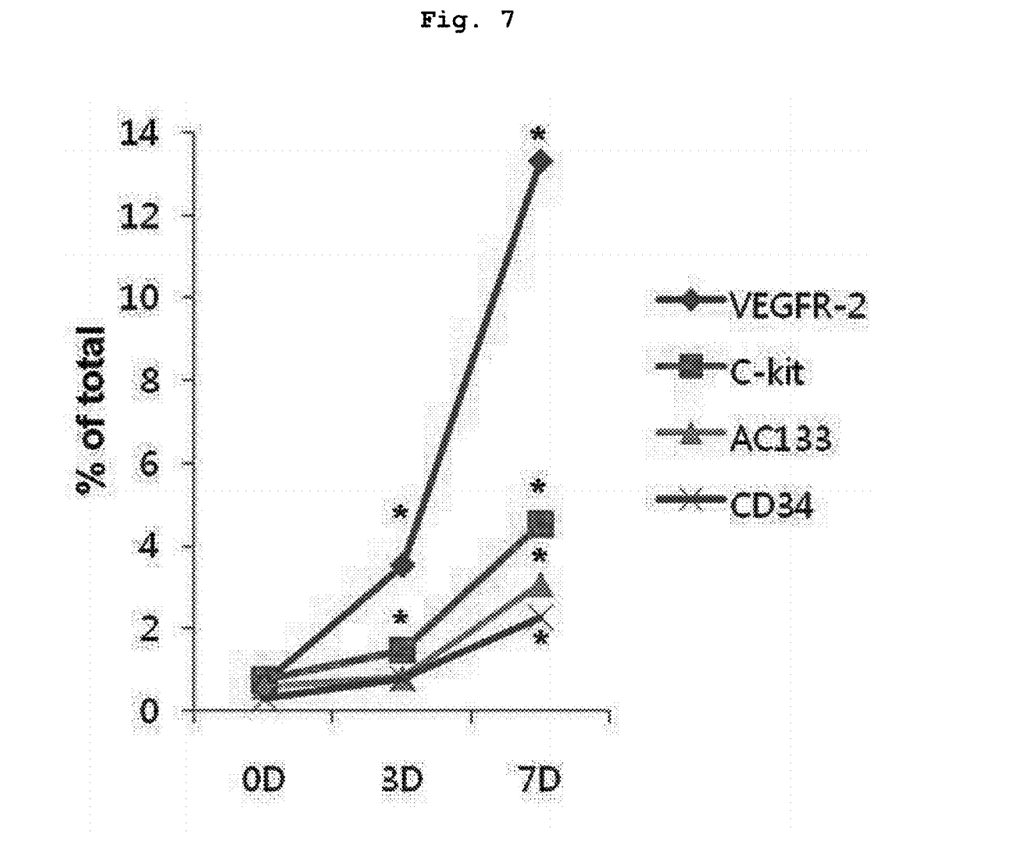

FIGS. 6 and 7 show the increase of cells positive to the marker of blood adult stem cells within the human blood-born hematospheres cultured by the method of the present invention. FIG. 6 shows immunofluorescence photographs of cells positive to various makers specific for stem cells in human blood-born hematospheres. FIG. 7 is a graph showing the proliferation of stem cell marker-positive cells within the human blood-born hematospheres, as measured by flow cytometry.

Figure 8:
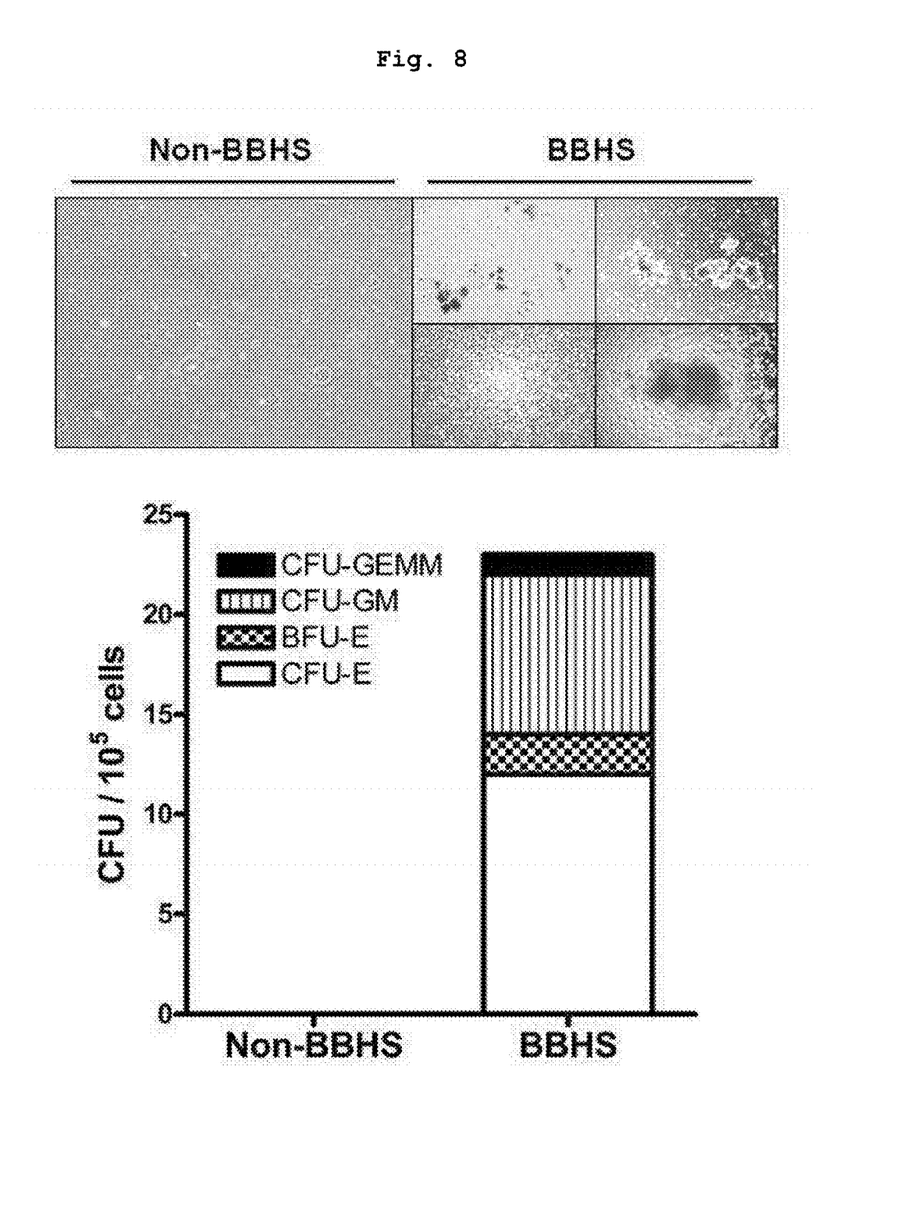
FIGS. 8 and 9 show in vitro and in vivo functionalities of blood adult stem cells within the human blood-born hematospheres cultured by the method of the present invention, respectively.
Figure 9:
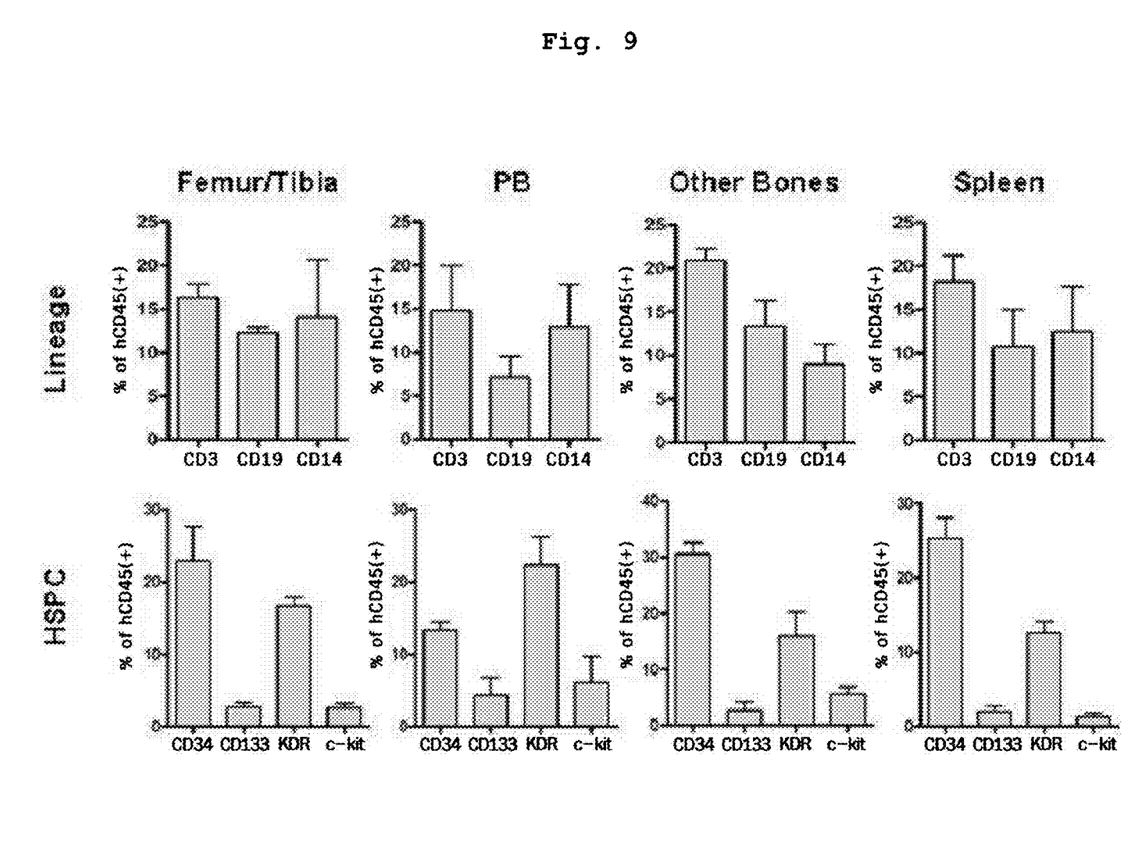

FIGS. 8 and 9 show in vitro and in vivo functionalities of the blood adult stem cells within the human blood-born hematospheres cultured by the method of the present invention, respectively. FIG. 8 shows results of the colony formation of blood cells on solid plates. FIG. 9 shows the chimerism of human blood cells in the blood organ of immune deficient mice after the stem cells obtained from human blood-born hematospheres are transplanted into the mice.

The above detailed descriptions of embodiments of the invention are not intended to be exhaustive or to limit the invention to the precise form disclosed above. While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application.

Industrial Applicability

Capable of allowing for the maximization of stem cell potency and for the in vitro production of stem cells, as described hitherto, the method of the present invention suggests a solution to ethical and economic problems encountered upon repeated bone marrow harvesting or blood sampling following G-CSF injection and it can be widely used in the medical area for the practical and economic value.

We claim:

1. A method for proliferating blood adult stem cells using human blood-born hematospheres, comprising:
   isolating mononuclear cells from blood;
   aggregate culturing the isolated cells in a three-dimensional structure;
   proliferating the three-dimensionally cultured cells to form blood-born hematospheres; and
   dissociating the blood-born hematospheres into single cells;
   wherein the blood adult stem cells are contained and proliferated within the blood-born hematospheres.

2. The method of claim 1, wherein the isolating step is carried out by:
   diluting 10 ml of blood in 25 ml of PBS (phosphate buffered saline) at room temperature to prevent blood coagulation;
   placing 35 ml of the blood dilution in 12 ml of Ficoll-Paque™ PLUS sterile medium; and
   centrifuging at room temperature for 30 min at 400×g with a brake off, to form a mononuclear cell layer and carefully removing the mononuclear cell layer.

3. The method of claim 1, wherein the aggregate culturing step is carried out by:
   removing blood residuals and platelets from the isolated cells by washing the isolated cells with 50 ml of PBS per 10 ml of the initial blood sample volume, and then spinning down to generate a pellet of washed cells; and
   suspending the pellet of washed cells in endothelial basal medium (EMB) free of serum, in EMB supplemented with 5% fetal bovine serum (FBS), or in a cell culture medium free of animal-derived components selected from the group consisting of Stemline II hematopoietic stem cell expansion medium, Stempro34 serum-free medium, and mTeSR®1 feeder-free cell culture medium.

4. The method of claim 3, wherein the suspended cells are cultured to maintain a high-density of $3\sim5\times10^6$ cells/ml in an ultra-low attach culture dish.

5. The method of claim 1, wherein the dissociating step is carried out by collecting the cell culture medium and the hematospheres in a tube, spinning the blood-born hematospheres down at 1,500 rpm for 10 min, exposing the hematospheres to PBS containing 0.125% trypsin-EDTA and 0.5 mg/ml dispase at 37° C. for 5 min, and centrifuging to obtain single cells.

* * * * *